United States Patent [19]

Pinchuk et al.

[11] Patent Number: 5,700,269
[45] Date of Patent: Dec. 23, 1997

[54] ENDOLUMINAL PROSTHESIS DEPLOYMENT DEVICE FOR USE WITH PROSTHESES OF VARIABLE LENGTH AND HAVING RETRACTION ABILITY

[75] Inventors: Leonard Pinchuk, Miami; Kevin J. Clair, Pembroke Pines, both of Fla.

[73] Assignee: Corvita Corporation, Miami, Fla.

[21] Appl. No.: 556,408

[22] Filed: Nov. 13, 1995

Related U.S. Application Data

[63] Continuation-in-part of Ser. No. 466,934, Jun. 6, 1995.

[51] Int. Cl.⁶ .................................................. A61B 19/00
[52] U.S. Cl. ............................................. 606/108; 606/198
[58] Field of Search ........................... 606/108, 198, 606/194, 191, 195, 190; 623/1, 12; 604/104, 105, 106, 107, 108, 109

[56] References Cited

U.S. PATENT DOCUMENTS

| | | |
|---|---|---|
| 1,920,495 | 8/1933 | Brown et al. . |
| 2,836,181 | 5/1958 | Tapp . |
| 2,977,839 | 4/1961 | Koch ............................ 87/1 |
| 3,095,017 | 6/1963 | Bleiler et al. . |
| 3,105,492 | 10/1963 | Jeckel ......................... 128/334 |
| 3,272,204 | 9/1966 | Artandi et al. . |
| 3,304,557 | 2/1967 | Polansky ......................... 3/1 |
| 3,317,924 | 5/1967 | Le Veen et al. . |
| 3,463,158 | 8/1969 | Schmitt et al. . |
| 3,479,670 | 11/1969 | Medell . |
| 3,485,234 | 12/1969 | Stevens ........................ 128/2 |
| 3,509,883 | 5/1970 | Diebelius . |
| 3,526,906 | 9/1970 | De Laszlo . |
| 3,562,820 | 2/1971 | Braun . |

(List continued on next page.)

FOREIGN PATENT DOCUMENTS

| | | |
|---|---|---|
| 0 587 197 | 10/1991 | European Pat. Off. . |
| 1 602 513 | 1/1970 | France . |
| 30 19 996 | 12/1981 | Germany . |
| 1 205 743 | 9/1970 | United Kingdom . |
| 2 015 118 | 9/1979 | United Kingdom . |
| 2 033 233 | 5/1980 | United Kingdom . |
| 2 077 107 | 12/1981 | United Kingdom . |
| 2 135 585 | 3/1986 | United Kingdom . |
| WO88/00813 | 2/1988 | WIPO . |
| WO91/12779 | 9/1991 | WIPO . |
| WO94/24961 | 11/1994 | WIPO . |

OTHER PUBLICATIONS

"A Study of the Geometrical and Mechanical Properties of a Self–Expanding Metallic Stent . . . " Jedwab et al, Jour. of Applied Biomaterials, Vo. 4, pp. 77–85 1993.

"Oesophageal Strictures" Didcott, Annals of the Royal Cllege of Surgeons of England, vol. 55, pp. 112–126, Aug. 1973.

*Primary Examiner*—Robert A. Hafer
*Assistant Examiner*—Benjamin Koo
*Attorney, Agent, or Firm*—David P. Gordon

[57] ABSTRACT

An endoluminal prosthesis deployment device includes a hollow plunger which is slideably mounted on a narrow inner catheter and an outer sheath through which the catheter and the plunger are slideable. The distal end of the plunger is provided with a soft retractor bulb and the distal end of the inner catheter is provided with a dilator tip. The proximal end of the plunger is provided with a locking mechanism for temporarily locking the relative positions of the plunger and the catheter and the proximal end of the outer sheath is provided with a locking mechanism for temporarily locking the relative positions of the plunger and outer sheath. The deployment device according to the invention accommodates protheses of different length by adjusting the distance between the distal end of the plunger and the dilator tip. This distance is adjusted by moving the plunger and/or the catheter relative to each other and locking their relative positions with the locking mechanism on the plunger. In addition, the retractor bulb provides a secure coupling of the distal end of the plunger to the proximal end of an endoluminal prosthesis such that the prosthesis may be retracted back into the outer sheath even after it is 80% deployed.

15 Claims, 5 Drawing Sheets

U.S. PATENT DOCUMENTS

| | | | |
|---|---|---|---|
| 3,580,289 | 5/1971 | James, Jr. | 138/121 |
| 3,585,707 | 6/1971 | Stevens . | |
| 3,626,947 | 12/1971 | Sparks . | |
| 3,710,777 | 1/1973 | Sparks . | |
| 3,730,835 | 5/1973 | Leeper . | |
| 3,822,238 | 7/1974 | Blair et al. | 260/75 |
| 3,868,956 | 3/1975 | Alfidi et al. . | |
| 3,878,565 | 4/1975 | Sauvage . | |
| 3,929,126 | 12/1975 | Corsaut . | |
| 3,974,526 | 8/1976 | Dardik et al. . | |
| 3,993,078 | 11/1976 | Bergentz et al. . | |
| 4,044,404 | 8/1977 | Martin et al. . | |
| 4,086,665 | 5/1978 | Poirier . | |
| 4,106,129 | 8/1978 | Carpentier et al. . | |
| 4,130,904 | 12/1978 | Whalen . | |
| 4,134,402 | 1/1979 | Mahurkar . | |
| 4,140,126 | 2/1979 | Choudhury . | |
| 4,164,045 | 8/1979 | Bokros et al. . | |
| 4,173,689 | 11/1979 | Lyman et al. . | |
| 4,193,138 | 3/1980 | Okita . | |
| 4,323,071 | 4/1982 | Simpson et al. . | |
| 4,355,426 | 10/1982 | MacGregor . | |
| 4,441,215 | 4/1984 | Kaster . | |
| 4,459,252 | 7/1984 | MacGregor . | |
| 4,475,972 | 10/1984 | Wong . | |
| 4,503,569 | 3/1985 | Dotter . | |
| 4,583,968 | 4/1986 | Mahurkar . | |
| 4,610,688 | 9/1986 | Silvestrini et al. . | |
| 4,655,771 | 4/1987 | Wallsten . | |
| 4,692,141 | 9/1987 | Mahurkar . | |
| 4,731,073 | 3/1988 | Robinson . | |
| 4,743,251 | 5/1988 | Barra . | |
| 4,787,899 | 11/1988 | Lazarus . | |
| 4,850,999 | 7/1989 | Planck . | |
| 4,871,357 | 10/1989 | Hsu . | |
| 4,875,480 | 10/1989 | Imbert | 128/343 |
| 4,878,906 | 11/1989 | Lindemann et al. | 623/1 |
| 4,895,561 | 1/1990 | Mahurkar | 604/43 |
| 4,935,006 | 6/1990 | Hasson | 604/43 |
| 4,954,126 | 9/1990 | Wallsten | 606/36 |
| 5,019,090 | 5/1991 | Pinchuk | 606/194 |
| 5,026,377 | 6/1991 | Burton et al. | 606/108 |
| 5,061,275 | 10/1991 | Wallsten et al. | 623/1 |
| 5,064,435 | 11/1991 | Porter | 623/12 |
| 5,078,720 | 1/1992 | Burton et al. | 606/108 |
| 5,116,360 | 5/1992 | Pinchuk et al. | 623/1 |
| 5,160,341 | 11/1992 | Brenneman et al. | 606/198 |
| 5,188,593 | 2/1993 | Martin | 604/43 |
| 5,197,978 | 3/1993 | Hess | 623/1 |
| 5,201,757 | 4/1993 | Heyn et al. | 606/198 |
| 5,234,437 | 8/1993 | Sepetka | 606/108 |
| 5,235,966 | 8/1993 | Jamner | 128/20 |
| 5,242,399 | 9/1993 | Lau et al. | 604/104 |
| 5,279,561 | 1/1994 | Roucher et al. | 604/96 |
| 5,290,295 | 3/1994 | Querals et al. | 606/108 |
| 5,312,415 | 5/1994 | Palermo | 606/108 |
| 5,330,500 | 7/1994 | Song | 606/198 |
| 5,360,397 | 11/1994 | Pinchuk | 604/27 |
| 5,383,892 | 1/1995 | Cardon et al. | 606/198 |
| 5,395,390 | 3/1995 | Simon et al. | 606/198 |
| 5,397,355 | 3/1995 | Marin et al. | 623/12 |
| 5,405,378 | 4/1995 | Strecker | 623/1 |
| 5,411,507 | 5/1995 | Heckele | 606/108 |
| 5,415,664 | 5/1995 | Pinchuk | 606/108 |
| 5,433,723 | 7/1995 | Lindenberg et al. | 606/198 |
| 5,464,408 | 11/1995 | Duc | 606/108 |

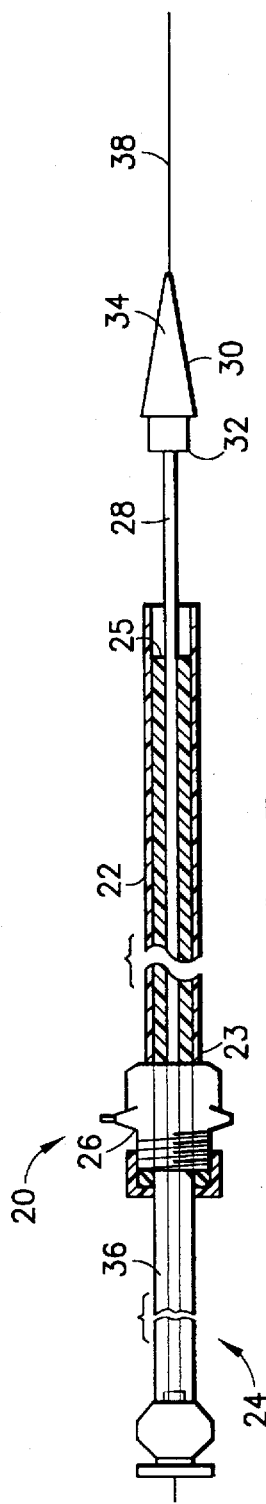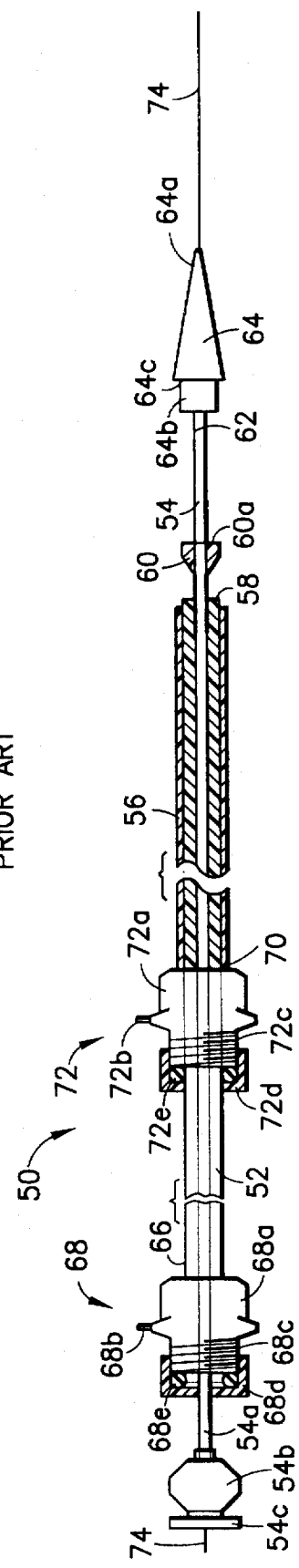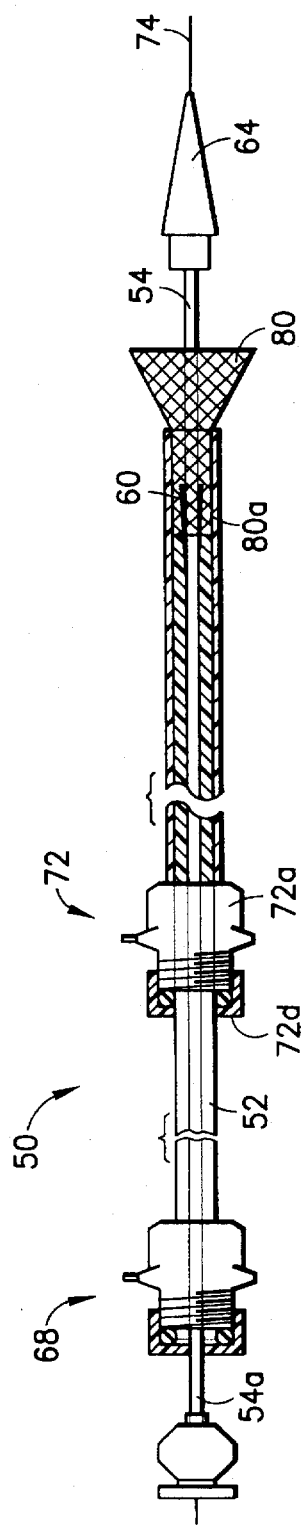
FIG. 3 PRIOR ART
FIG. 4
FIG. 5

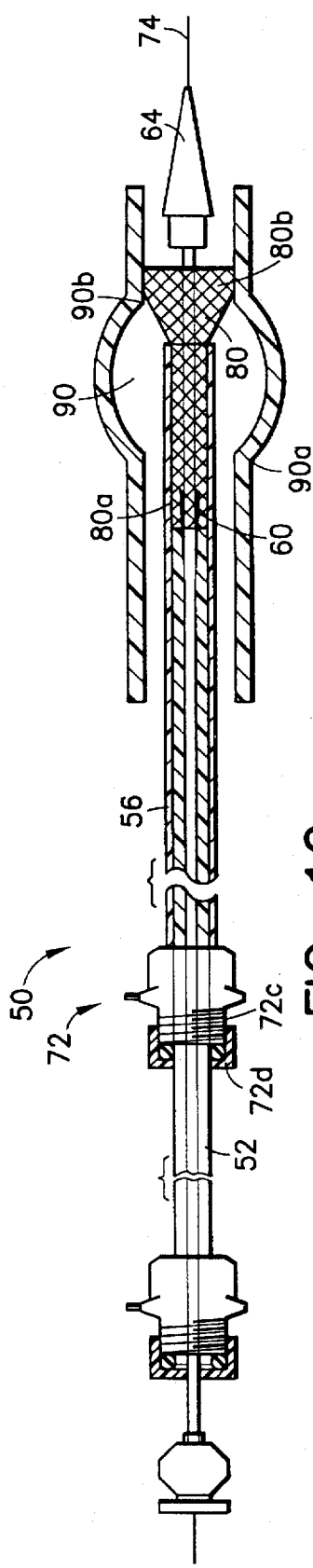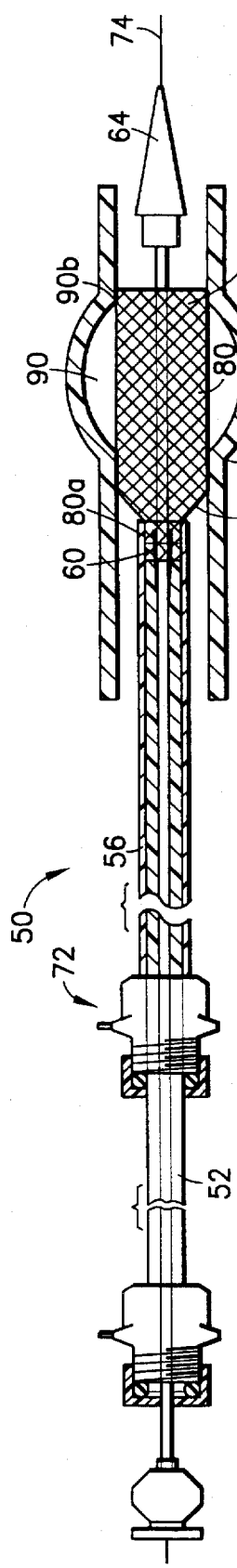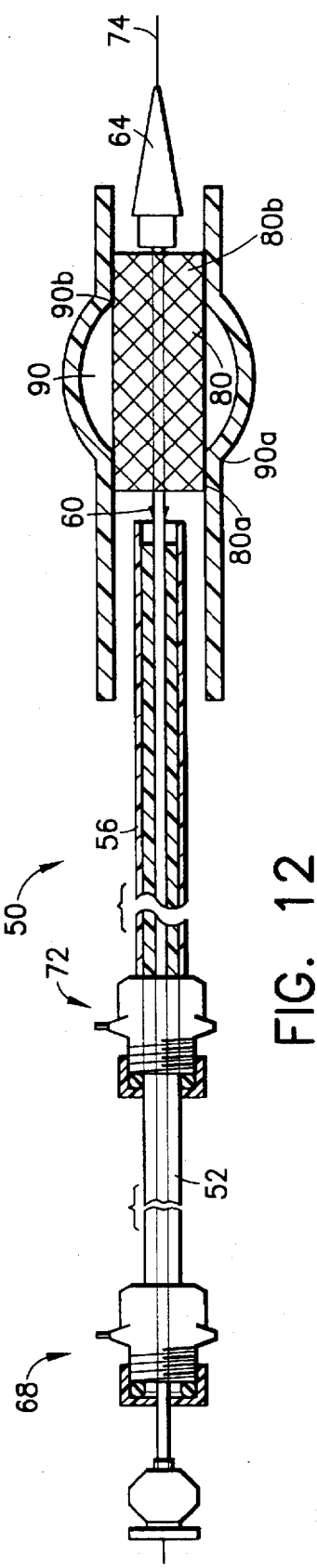

ENDOLUMINAL PROSTHESIS DEPLOYMENT DEVICE FOR USE WITH PROSTHESES OF VARIABLE LENGTH AND HAVING RETRACTION ABILITY

This application is a continuation-in-part of Ser. No. 08/466,934 filed Jun. 6, 1995.

BACKGROUND OF THE INVENTION

1. Field of the Invention

The invention relates to devices for deploying endoluminal prostheses. More particularly, the invention relates to a deployment device which accommodates prostheses of different lengths and which allows retraction of a prosthesis prior to full deployment.

2. State of the Art

Transluminal prostheses are well known in the medical arts for implantation in blood vessels, biliary ducts, or other similar organs of the living body. These prostheses are commonly known as stents and are used to maintain, open, or dilate tubular structures or to support tubular structures that are being anastomosed. When biocompatible materials are used as a covering or lining for the stent, the prosthesis is called a stent-graft. If used specifically in blood vessels, the stent-graft is known as an endovascular graft. A stent or stent-graft may be introduced into the body by stretching it longitudinally or compressing it radially, until its diameter is reduced sufficiently so that it can be fed into a catheter. The stent-graft is delivered through the catheter to the site of deployment and then released from the catheter, whereupon it self-expands. Stent-grafts introduced in this manner are known as endoluminal stent-grafts.

A typical state of the art stent, such as disclosed in U.S. Pat. No. 4,655,771 to Wallsten or in U.K. Patent Number 1,205,743 to Didcott, is shown herein in prior art FIGS. 1, 1a, 2, and 2a. Didcott and Wallsten disclose a tubular body stent 10 composed of wire elements 12, each of which extends in a helical configuration with the centerline 14 of the stent 10 as a common axis. Half of the elements 12 are wound in one direction while the other half are wound in an opposite direction. With this configuration, the diameter of the stent is changeable by axial movement of the ends 9, 11 of the stent. Typically, the crossing elements form a braid-like configuration and are arranged so that the diameter of the stent 10 is normally expanded as shown in FIGS. 1 and 1a. The diameter may be contracted by pulling the ends 9, 11 of the stent 10 away from each other as shown by the arrows 16, 18 in FIG. 2. When the ends of the body are released, the diameter of the stent 10 self-expands and draws the ends 9, 11 of the stent closer to each other. The contraction to stretching ratio and radial pressure of stents can usually be determined from basic braid equations. A thorough technical discussion of braid equations and the mechanical properties of stents is found in Jedweb, M. R. and Clerc, C. O., "A Study of the Geometrical and Mechanical Properties of a Self-Expanding Metallic Stent-Theory and Experiment", *Journal of ADDlied Biomaterials*; Vol. 4, pp. 77–85 (1993).

The fact that stents undergo various dimension changes from their compressed form to their uncompressed form, results in complications in placement. Placement of a stent having any degree of elongation and radial force as a result of compression is very difficult for several reasons. First, the stent, depending on its pitch angle, may have to be pushed out of the catheter over a long distance. This may be extremely difficult in light of the increased friction forces and various bent sections encountered in the catheter as it traverses a tortuous path. Second, the stent may conversely shrink significantly in length as its diameter expands, thereby rendering it difficult to accurately place it in a vessel. Third, plaque, thrombus or other protrusions or inclusions in the blood vessel lumen may alter the diameter of the stent which consequently alters the length of the stent. The importance of extreme accuracy in placement of an endovascular graft (EVG) will be appreciated by those knowledgeable in the art. For example, in aneurysmal vessel disease, such as that encountered in the abdominal aorta where the distance between the renal arteries and the aneurysm is quite short (less than 3 cm), misplacement of an EVG over the renal arteries or only in the aneurysm can prove fatal.

Proper placement of the stent becomes impossible where the stent is too long or too short for the body cavity in which it is being deployed. In order to be effective, the dimensions of a vessel must be known very accurately and the stent must be tailored to match the specifications of the vessel.

Several difficulties arise, however, when trying to determine the proper stent length needed for any particular cavity. One such problem, especially present with the self expanding stent design such as described by Wallsten and Didcott, is that it is often difficult to predict exactly to what length the stent should be cut in order to properly fit within a particular blood vessel. For example, when deploying an EVG in an aortic aneurysm, the distal end of the stent may reside in the aneurysmal area if the stent is cut too short in length, thereby not sealing the aneurysm and causing potential problems, such as rupturing of the aneurysm. On the other hand, if the EVG is cut too long, the distal end of the EVG can extend into one of the iliac arteries which will lead to clotting of the contralateral iliac artery. Also, if deployed in a vessel with multiple branching, and EVG which is too long may inadvertently cover an arterial branch, thereby occluding the branch and starving the organ which it is intended to nourish.

It is known to presently approximate the deployment length of an EVG stent by using various angiographical techniques (x-ray examinations of blood vessels or lymphatics following the injection of a radiopaque substance). In particular, this is done by injecting radiopaque dye into a vessel and photographing the dye with an X-ray machine as it moves through the vessel. It is also known to use Computerized Tomography (CT) scans and the like to show arterial diameters from which the desired deployment stent length can be extrapolated. Other more novel methods for visualizing vessels include spiral CT scan and intravascular ultrasound (IVUS). Parent application Ser. No. 08/466,934 discloses an apparatus and a method for measuring the desired length of a prosthetic device which is to be implanted in a body cavity of a patient. The apparatus generally includes a plunger which is connected to the proximal end of a stent and a sheath which slides over the plunger and stent. A proximal portion of the plunger is provided with a scale for measuring an indication of the length of the stent which is removably deployed in the body cavity. Proximal movement of the sheath to partially deploy the stent causes a length to be indicated on the scale. The stent is placed and partially deployed within the body cavity using the plunger and sheath. Once the stent bridges the body cavity, the scale is used to determine the length of the deployed portion of the stent. The stent is retracted into the sheath and the apparatus is then removed from the body cavity. The indicated length is used to cut a stent for implantation using a conventional stent introducer.

Prior art FIG. 3 shows a conventional stent introducer 20 having an outer sheath 22 and a plunger 24 which is movable through the sheath. The proximal end 23 of the sheath 22 is provided with a locking mechanism 26 for reversibly locking the relative positions of the sheath 22 and the plunger 24. A narrow catheter 28 extends from the distal end 25 of the plunger 24 and terminates with a dilator tip 30. The dilator tip 30 typically has a cylindrical proximal end and a conically tapered distal end 34. A continuous lumen 36 extends through the plunger 24, the catheter 28, and the dilator tip 30 so that the entire instrument 20 may be carried on a guide wire 38 to the site of implantation. A stent (not shown) is placed into the introducer by radially compressing and axially expanding (elongating) the stent in the space between the distal end 25 of the plunger and the proximal end 32 of the dilator tip 30 and by sliding the sheath 22 over the stent. After the introducer 20 is guided to the implantation site with the aid of the guide wire 38, the plunger 24 is held stationary, the sheath 22 is pulled proximally, and the stent is released from the sheath 22.

It is a noteworthy limitation of the introducer 20 that the length of the catheter 28, and thus the distance between the distal end 25 of the plunger 24 and the proximal end 32 of the dilator tip 30, is fixed. Therefore, the introducer 20 will only accommodate stents have an axially expanded length substantially the same as the length of the catheter 28. Thus, during an implantation procedure where a stent may have to be trimmed to size, many different sized introducers must be kept on hand, and more than one introducer may have to be used. It is also noteworthy that the introducer 20, and in particular the plunger 24 has no provisions for attaching to the stent in any way. Therefore, as the stent is being deployed, there is no way to reverse the deployment process. Once the stent has expanded radially a sufficient amount to engage the wall of a vessel it cannot be relocated and cannot be drawn back into the sheath.

SUMMARY OF THE INVENTION

It is therefore an object of the invention to provide an endoluminal prosthesis deployment device which is adjustable for use with prostheses of different lengths.

It is also an object of the invention to provide an endoluminal prosthesis deployment device which allows retraction of the prosthesis during deployment.

In accord with these objects which will be discussed in detail below, an endoluminal prosthesis deployment device according to the present invention includes a hollow plunger which is slideably mounted on a narrow inner catheter and an outer sheath through which the catheter and the plunger are slideable. The distal end of the plunger is provided with a soft retractor bulb and the distal end of the inner catheter is provided with a dilator tip. The proximal end of the plunger is provided with a locking mechanism for temporarily locking the relative positions of the plunger and the catheter, and the proximal end of the outer sheath is provided with a locking mechanism for temporarily locking the relative positions of the plunger and outer sheath. The deployment device according to the invention accommodates prostheses of different length by adjusting the distance between the distal end of the plunger and the dilator tip. This distance is adjusted by moving the plunger and/or the catheter relative to each other and locking their relative positions with the locking mechanism on the plunger. In addition, the retractor bulb provides a secure coupling of the distal end of the plunger to the proximal end of an endoluminal prosthesis such that the prosthesis may be retracted back into the outer sheath even after it is 80% deployed.

The retractor bulb is preferably made of a soft, tear-resistant material which is molded in a conical or frustroconical shape with its base at its distal end. The diameter of the base of the bulb is preferably between 0.005" greater than the inner diameter of the sheath and 0.002" less than the inner diameter of the sheath. The distance between the base of the bulb and the distal end of the plunger is preferably between 0.1" and 0.25". Suitable materials for the retractor bulb include soft resilient materials, such as those with hardnesses in the Shore 30A to Shore 55D range such as polyurethane, silicone rubber, polyolefin, sponge rubber, hydrogel, pebax nylon, glycolated polyester, etc. The catheter, plunger, and sheath are preferably made of polyethylene, polyamide, TEFLON, FEP, polyolefin, polyester, etc. with material Shore hardnesses preferably within the range of Shore 70A to Shore 100D.

According to a preferred aspect of the invention, the locking mechanisms on the plunger and the sheath are provided with hemostasis valves and flush ports so that the annular spaces between the catheter and the plunger and between the plunger and the sheath can be flushed with heparinized saline.

Additional objects and advantages of the invention will become apparent to those skilled in the art upon reference to the detailed description taken in conjunction with the provided figures.

BRIEF DESCRIPTION OF THE DRAWINGS

FIG. 3 is a broken transparent side elevation view in partial section of a prior art stent introducer;

FIG. 4 is a broken transparent side elevation view in partial section of a deployment device according to the invention;

FIGS. 5–7 are views similar to FIG. 4 of a device according to the invention in preparatory stages of operation wherein a stent is loaded into the device for eventual deployment;

FIGS. 10–12 are broken transparent side elevation views in partial section of a device according to the invention during first, second, and third stages of deploying a stent.

DETAILED DESCRIPTION OF THE PREFERRED EMBODIMENTS

Figure 1:
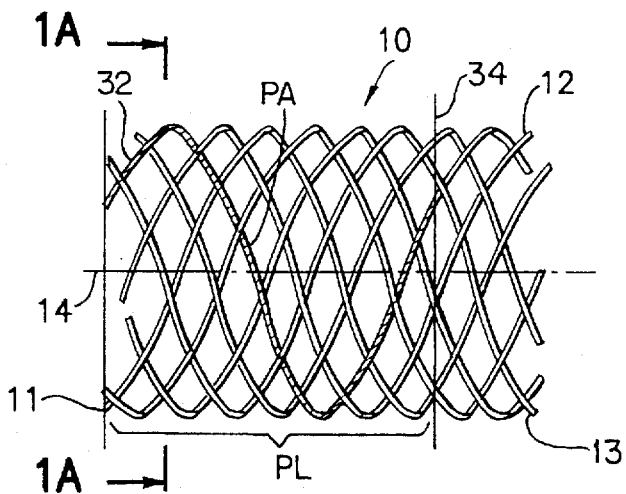
FIG. 1 is a broken side elevation view of a prior art stent expanded in a non-stressed position.
Figure 1A:
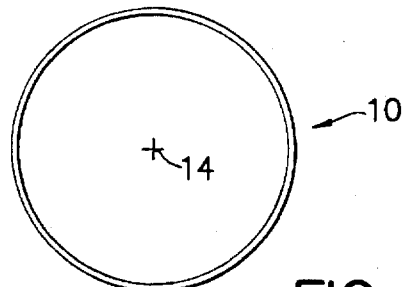
FIG. 1a is a cross sectional view along line 1A—1A of FIG. 1.
Figure 2:
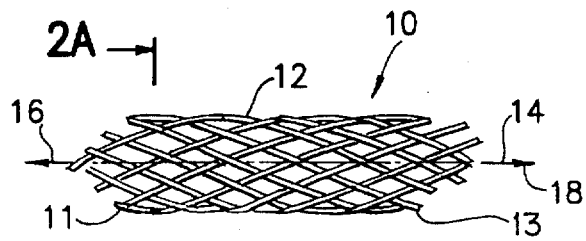
FIG. 2 is a broken side elevation view of a prior art stent stretched and contracted.
Figure 2A:
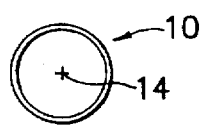
FIG. 2a is a cross sectional view along line 2A—2A of FIG. 2.

Referring now to FIG. 4, an endoluminal prosthesis deployment device 50 according to the present invention includes a hollow plunger 52 which is slideably mounted on a narrow inner catheter 54 and an outer sheath 56 through which the catheter 54 and the plunger 52 are slideable. The plunger 52, catheter 54, and sheath 56 are preferably made of polyethylene, polyamide, TEFLON, FEP, polyolefin, polyurethane, polyester, etc. The distal end 58 of the plunger 52 is provided with a soft retractor bulb 60 and the distal end 62 of the inner catheter 54 is provided with a dilator tip 64. The dilator tip 64 has a distal frustroconical portion 64a and a proximal cylindrical portion 64b defining a step 64c therebetween, and is preferably constructed from any of the materials mentioned above with respect to the retractor bulb and the catheter. The proximal end 66 of the plunger 52 is provided with a locking mechanism 68 for temporarily locking the relative positions of the plunger 52 and the catheter 54, and the proximal end 70 of the outer sheath 56 is provided with a locking mechanism 72 for temporarily locking the relative positions of the plunger 52 and outer sheath 56.

The retractor bulb 60 is preferably made of a soft, tear-resistant material which is molded in a conical or frustroconical shape with its base 60a at its distal end. The diameter of the base 60a of the bulb 60 is preferably between 0.005" greater than the inner diameter of the sheath 56 and 0.002" less than the inner diameter of the sheath 56. The retractor bulb 60 is positioned at the distal end of the plunger 52 so that the distance between the base 60a of the bulb 60 and the distal end 58 of the plunger 52 is preferably between 0.05" and 0.375". Suitable materials for the retractor bulb 60 include polyurethane, silicone rubber, polyolefin, sponge rubber, hydrogel, pebax nylon, glycolated polyester, etc. of hardnesses in the Shore 30A to Shore 55D range.

From the foregoing, it will be appreciated that the distance between the bulb 60 and the dilator tip 64 may be adjusted and temporarily locked in order to accommodate different length stents.

The locking mechanisms 68 and 72 each preferably include a body 68a, 72a having a fluid side port 68b, 72b, a proximal threaded end 68c, 72c, a threaded cap 68d, 72d, and an O-ring 68e, 72e between the cap 68d, 72d, and the proximal end 68c, 72c of the body 68a, 72a. Tightening the caps 68d, 72d compresses the O-rings 68e, 72e to form mechanical and fluid seals between the plunger 52 and the catheter 54 and between the sheath 56 and the plunger 52, respectively. Preferably, the O-rings maintain a fluid seal even when the caps are loosened.

The proximal end 54a of the catheter 54 is preferably provided with a hub 54b, a luer lock 54c, and a passageway (not shown) which receives a guide wire 74. The device 50 is intended to be used in conjunction with a guide wire 74 as described in detail below.

Figure 6:
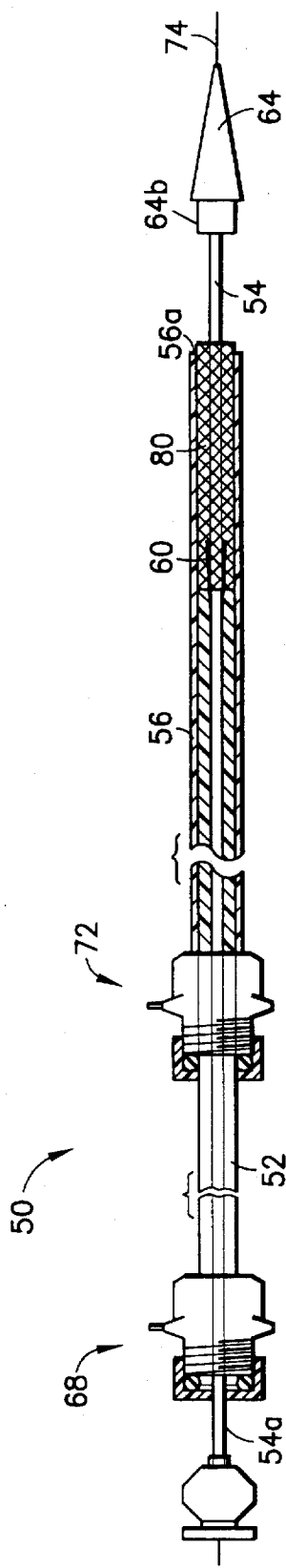
Figure 7:
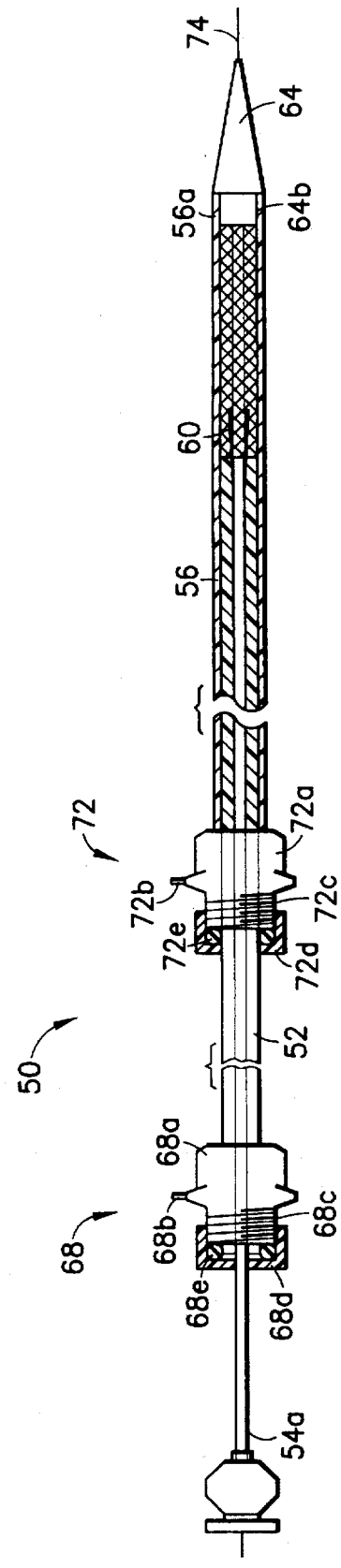

Turning now to FIGS. 5–7, the deployment device 50 according to the invention is "loaded" with a stent or other endoluminal prosthesis 80 which is previously cut to the desired length. The proximal end 80a of the prosthesis is placed over the retractor bulb 60 and the prosthesis is stretched so that the diameter of the proximal end is reduced to fit inside the sheath 56. The plunger 52 and/or the sheath 56 are moved away from each other so that the bulb 60 is drawn inside the sheath 56 with the proximal end 80a of the prosthesis 80 being captured between the bulb 60 and the interior of the sheath 56 as shown in FIG. 5. The plunger 52 and/or the sheath 56 are moved farther away from each other until the prosthesis 80 is substantially contained within the sheath 56 as shown in FIG. 6. After the prosthesis 80 is completely within the sheath 56, the proximal end 64b of the dilator tip 64 is drawn into the distal end 56a of the sheath 56, as shown in FIG. 7, by moving the plunger 52 and/or the catheter 54 away from each other. When the device 50 is loaded with the prosthesis 80 as shown in FIG. 7, the caps 68d, 72d of the respective locking mechanisms 68, 72 are tightened so that the relative positions of the plunger, 52, catheter 54, and sheath 56 are locked. Utilizing the fluid ports 68b, 72b, the annular spaces between the plunger and the catheter and between the plunger and the sheath are flushed with heparinized saline. Grooves or channels (not shown) in the cylindrical section 64b of the dilator tip 64 extending from the most proximal end of the dilator tip 64 to the step 64c allow fluid to exit the space between the plunger 52 and the sheath 56, and between the plunger 52 and the catheter 54 during the flushing procedure. The device 50 is then ready for introduction into the human body.

Figure 8:
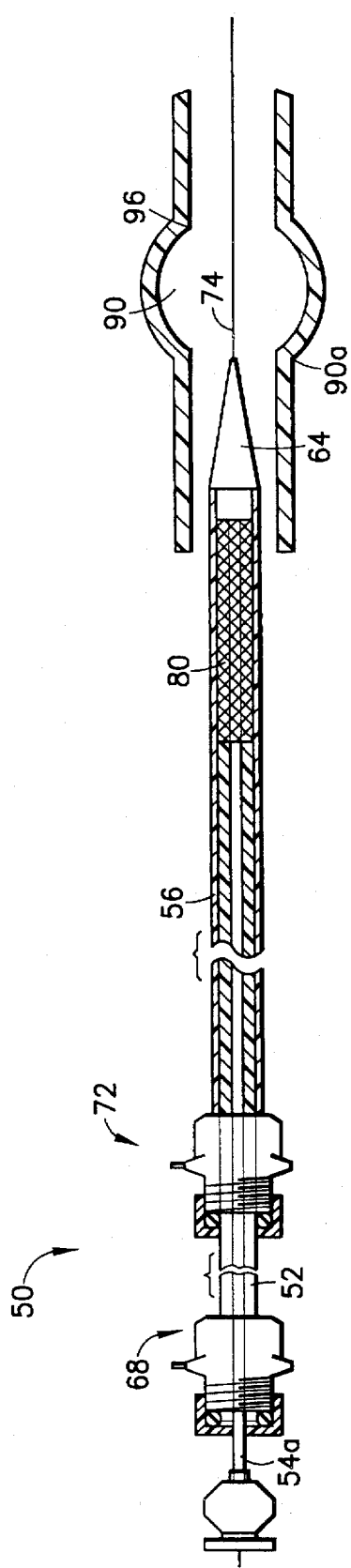
FIGS. 8 and 9 are views similar to FIG. 7 of a device according to the invention being located at the site of an aneurysm with the aid of a guide wire.
Figure 9:
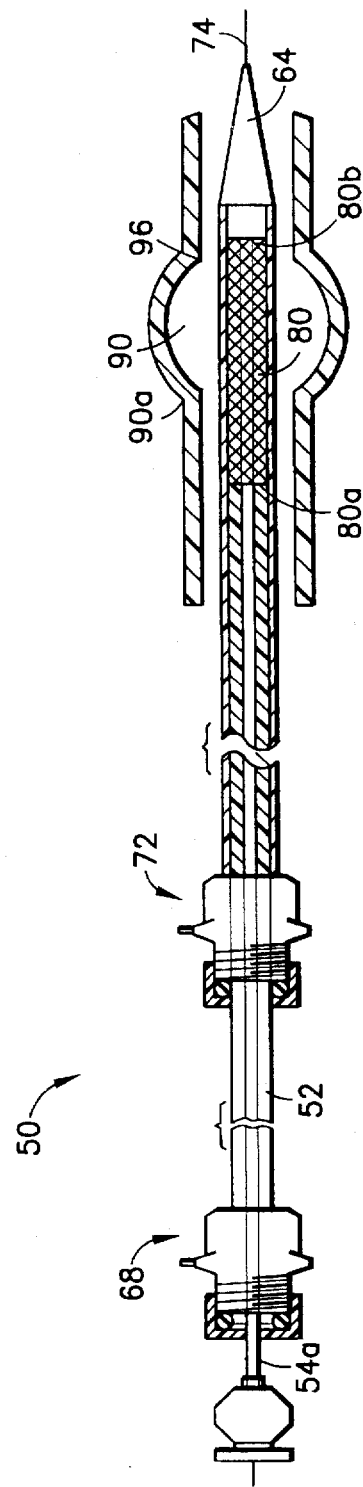

Referring now to FIGS. 8 and 9, the deployment device 50 according to the invention is guided to a surgical site (e.g. aneurysm) 90 with the aid of a guide wire 74 which is inserted through the lumen of the catheter 54. The practitioner can monitor the progress of the deployment using a fluoroscope and radiopaque media which is carried and disseminated alongside the device 50 as it travels through the patient. In addition, the device 50 and prosthesis 80 are themselves preferably radiopaque, thereby further aiding visualization under fluoroscopy. The device 50 is located as shown in FIG. 9, with the prosthesis 80 spanning the aneurysm 90 such that the proximal end 80a of the prosthesis 80 is located proximal of the proximal neck 90a of the aneurysm 90 and the distal end 80b of the prosthesis 80 is located distal of the distal neck 90b of the aneurysm 90. When the device 50 is so located, the prosthesis 80 may be deployed.

Turning now to FIGS. 10–12, deployment of the prosthesis 80 is effected by loosening the cap 72d of the locking mechanism 72 so that the plunger 52 and the sheath 56 are movable relative to each other. While holding the plunger 52 stationary, the sheath 56 is moved proximally so that the distal end 80b of the prosthesis 80 is released as shown in FIG. 10. Those skilled in the art will appreciate that the distal end 80b of the prosthesis 80 should expand at a location distal of the distal neck 90b of the aneurysm 90. If the distal end 80b of the prosthesis 80 expands inside the aneurysm 90, the deployment process can be reversed by moving the sheath 56 in the distal direction to recapture the distal end of the prosthesis. After recapture, the device 50 may be relocated and deployment resumed. When the distal end 80b of the prosthesis 80 is expanded in the proper location, as shown in FIG. 10, the deployment process continues by moving the sheath 56 in the proximal direction so that substantially all of the prosthesis 80 is expanded as shown in FIG. 11. It is preferable at this point to refrain from releasing the proximal end 80a of the prosthesis 80 until it is ascertained that the proximal portion 80c of the prothesis 80 is properly located. Those skilled in the art will appreciate that the proximal end 80a of the prosthesis 80 should expand at a location proximal of the proximal neck 90a of the aneurysm 90. If, at this stage of deployment, it appears that the proximal end 80a of the prosthesis 80 will expand inside the aneurysm 90, the deployment process can be reversed by moving the sheath 56 in the distal direction to recapture the entire prosthesis 80 for relocation or for removal from the body and replacement with a different sized Prothesis. If, on the other hand, it appears that the prosthesis 80 is correctly located as shown in FIG. 11, the proximal end 80a of the prosthesis is released by moving the sheath 56 proximally until the bulb 60 is exposed and the proximal end 80a of the prosthesis exits the distal end of the sheath 56.

It will be appreciated that after the prosthesis 80 is deployed as shown in FIG. 12, the deployment device 50 is removed from the body typically with the aid of the guide wire 74. Prior to removing the device 50, it is preferable that the dilator tip 64 be retracted into the distal end of the sheath 56. This may be accomplished by moving the sheath distally, by moving the plunger proximally, or by releasing the locking mechanism 68 and moving the catheter proximally.

There have been described and illustrated herein an endoluminal prosthesis deployment device for use with prostheses of variable length and having retraction ability. While particular embodiments of the invention have been described, it is not intended that the invention be limited thereto, as it is intended that the invention be as broad in scope as the art will allow and that the specification be read likewise. Thus, while particular materials and material hardnesses have been disclosed, it will be appreciated that other materials and/or hardnesses could be utilized. Also, while particular locking mechanisms have been shown, it will be recognized that other types of locking mechanisms could be used with similar results obtained. Moreover, while a particular configuration has been disclosed in reference to the retractor bulb, it will be appreciated that other configurations could be used as well. For example, the retractor bulb could be inflatable, or might take the form of multi-jawed clamp. Furthermore, while the device has been disclosed as having fluid ports for flushing, it will be understood that similar devices which omit the fluid ports can achieve the same or similar function as disclosed herein. Further yet, those skilled in the art will appreciate that all sliding materials can be coated with lubricating agents such as hydrogels which provide slippery surfaces, silicone oils, and the like to help maneuver the catheter through tortuous paths and to remote locations in the body. It can also be appreciated that drugs such as anticoagulants, anti-inflammatories, bactericidics, and antibiotics can be incorporated into the surface of these delivery catheters to limit blood-clots, infection, and other deleterious events that may hinder the procedure. It will therefore be appreciatedby those skilled in the art that yet other modifications could be made to the provided invention without deviating from its spirit and scope as so claimed.

We claim:

1. An endoluminal prosthesis deployment device for use with an endoluminal prosthesis, said device comprising:
   a) an outer sheath having a proximal end and a distal end;
   b) an inner plunger having a proximal end and a distal end, said inner plunger slideably disposed within said outer sheath; and
   c) prosthesis gripping means on said distal end of said inner plunger for engaging a proximal end of a prosthesis and drawing the prosthesis into said distal end of said outer sheath without engaining the distal end of the prosthesis when the prothesis is completely drawn into said outer sheath, said prosthesis gripping means comprises a soft tear-resistant bulb.

2. A device according to claim 2, wherein:
said bulb has a substantially frustroconical distal end.

3. A device according to claim 3, wherein:
said distal end of said bulb has an outer diameter which is substantially the same as an inner diameter of said outer sheath.

4. A device according to claim 4, wherein:
said outer diameter is between 0.005" larger than said inner diameter and 0.002" smaller than said inner diameter.

5. A device according to claim 1, wherein:
said distal end of said gripping means is within 0.1" and 0.25" of said distal end of said plunger.

6. A device according to claim 1, further comprising:
   d) locking means coupled to one of said outer sheath and said inner plunger for releasably preventing said plunger from sliding within said sheath.

7. A device according to claim 7, wherein:
said locking means includes an O-ring and a fluid port, said fluid port being in fluid communication with an annular space between said sheath and said plunger.

8. An endoluminal prosthesis deployment device for use with an endoluminal prosthesis, said device comprising:
   a) an outer sheath having a proximal end and a distal end;
   b) an inner plunger having a proximal end and a distal end, said inner plunger slidably disposed within said outer sheath; and
   c) prosthesis gripping means on said distal end of said inner plunger for engaging a proximal end of a prosthesis and drawing the prosthesis into said distal end of said outer sheath without engaging the distal end of the prosthesis when the prosthesis is completely drawn into said outer sheath;
   d) an inner catheter having a proximal end and a distal end, said inner catheter being slideably disposed within said inner plunger;
   e) a tapered tip attached to said distal end of said inner catheter, said tapered tip being dimensioned to substantially cover said distal end of said outer sheath when said inner catheter is moved proximally relative to said outer sheath such that a prosthesis engained by said gripping means cannot be deployed without first moving said inner catheter distally.

9. A device according to claim 9, further comprising:
   f) locking means coupled to one of said inner plunger and said inner catheter for releasably preventing said inner catheter from sliding within said plunger.

10. A device according to claim 10, wherein:
said locking means includes an O-ring and a fluid port, said fluid port being in fluid communication with an annular space between said catheter and said plunger.

11. A device according to claim 10, further comprising:
   g) a catheter hub coupled to said proximal end of said catheter, said catheter hub including a luer connector.

12. An endoluminal prosthesis deployment device for use with an endoluminal prosthesis, said device comprising:
   a) an outer sheath having a proximal end and a distal end;
   b) a plunger having a proximal end and a distal end, said plunger slideably disposed within said outer sheath;
   c) an inner catheter having a proximal end and a distal end, said inner catheter being slideably disposed within said plunger; and
   d) a tapered tip attached to said distal end of said inner catheter, said tapered tip being dimensioned to substantially cover said distal end of said outer sheath when said inner catheter is moved proximallv relative to said outer sheath such that said distal end of said plunger cannot be moved distally beyond said distal end of said outer sheath without first moving said inner catheter distally.

13. A device according to claim 13, further comprising:
   e) locking means coupled to one of said plunger and said inner catheter for releasably preventing said inner catheter from sliding within said plunger.

14. A device according to claim 14, wherein:
said locking means includes an O-ring and a fluid port, said fluid port being in fluid communication with an annular space between said catheter and said plunger.

15. A device according to claim 13, further comprising:
   e) a catheter hub coupled to said proximal end of said catheter, said catheter hub including a luer connector.

* * * * *